United States Patent [19]
Juneau et al.

[11] Patent Number: 6,022,311
[45] Date of Patent: Feb. 8, 2000

[54] APPARATUS AND METHOD FOR A CUSTOM SOFT-SOLID HEARING AID

[75] Inventors: Roger P. Juneau, Destrehan; Lynn P. Creel, Kenner; Edward J. Desporte, Covington; Michael Major; Gregory R. Siegle, both of Kenner, all of La.

[73] Assignee: General Hearing Instrument, Inc., Harahan, La.

[21] Appl. No.: 09/084,864

[22] Filed: May 26, 1998

Related U.S. Application Data

[60] Provisional application No. 60/068,035, Dec. 18, 1997.

[51] Int. Cl.[7] .................................................. H04R 25/00
[52] U.S. Cl. ............................................ 600/25; 381/69
[58] Field of Search ............... 600/25; 607/55–57; 381/68.6, 69; 181/130, 135

[56] References Cited

U.S. PATENT DOCUMENTS

| | | |
|---|---|---|
| 4,051,330 | 9/1977 | Cole . |
| 4,375,016 | 2/1983 | Harada . |
| 4,607,720 | 8/1986 | Hardt . |
| 4,716,985 | 1/1988 | Haertl . |
| 4,811,402 | 3/1989 | Ward . |
| 4,870,688 | 9/1989 | Voroba et al. . |
| 4,880,076 | 11/1989 | Ahlberg et al. . |
| 4,937,876 | 6/1990 | Biërmans . |
| 5,002,151 | 3/1991 | Oliveira et al. . |
| 5,068,902 | 11/1991 | Ward . |
| 5,185,802 | 2/1993 | Stanton . |
| 5,201,007 | 4/1993 | Ward et al. . |
| 5,259,032 | 11/1993 | Perkins et al. . |
| 5,430,801 | 7/1995 | Hill . |
| 5,500,902 | 3/1996 | Stockham, Jr. et al. . |
| 5,530,763 | 6/1996 | Aebi et al. . |
| 5,659,621 | 8/1997 | Newton . |

FOREIGN PATENT DOCUMENTS 61-238198  10/1986  Japan .

OTHER PUBLICATIONS

Oliveira, Robert J., "The Active Ear", *Journal of American Academy of Audio1094*, Dec. 1997, pp. 401–410.

Staab, Wayne J. and Barry Finlay, "A fitting rationale for deep fitting canal hearing instruments", *Hearing Instruments*, vol. 42, No. 1, 1991, pp. 7–10, 48.

*Primary Examiner*—John P. Lacyk
*Attorney, Agent, or Firm*—Garvey, Smith, Nehrbass and Doody, LLC

[57] ABSTRACT

An apparatus and method of manufacturing a soft-solid elastomer custom ear device into which electronics can be embedded provides a completely in-the-ear hearing aid with a soft body. This technology can replace hard acrylic ear molding. This hearing aid by virtue of its soft-solid design, meets the needs of the dynamic human ear canal which cannot be met with conventional hard acrylic molding. This hearing aid provides improved comfort and sound quality by better adapting to the dynamic changes in the ear canal which occur during everyday activities. This soft custom body also provides for ear-worn configurations of all subminiature electronic devices requiring discrete coupling to the human ear. These devices include digital telephones, cellular telephones, pagers, two-way communication systems, clocks, recorders, and many other subminiature technologies.

29 Claims, 9 Drawing Sheets

APPARATUS AND METHOD FOR A CUSTOM SOFT-SOLID HEARING AID

CROSS-REFERENCE TO RELATED APPLICATIONS

Priority of U.S. Provisional patent application Ser. No. 60/068,035, filed Dec. 18, 1997, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

I. Field of the Invention

The present invention relates to an ear-worn device that is comprised of a soft yet solid elastomer corpus for use in custom in-the-ear hearing products. The degree of stiffness of this soft-solid material preferably ranges from negligible to forty points, Durometer Hardness, Shore A. Specifically, the present invention relates to a system and method for producing a custom soft yet solid elastomer hearing product yielding the user greater comfort and superior acoustic performance. Additionally, this product will provide solutions to a population previously unsuccessfully fit by traditional custom in-the-ear technology. By the nature of its soft design this product will better accommodate dynamic changes in the external ear canal, that is, jaw movement, tortuous ear canals, and individuals with severe hearing loss.

The field of mass communication is also addressed for future applications of this invention, such as an ear-worn digital telephone or two-way radio system.

II. Description of the Related Art

The Hearing Health Industry has enjoyed major advancements in electronic design. The on-going miniaturization of electronics has brought the industry from a table worn unit, using vacuum tubes in the nineteen twenties, to a wearable body worn unit in the late nineteen thirties. With the introduction of transistors in the nineteen fifties, behind-the-ear (BTE) hearing aids became possible. As integrated circuits were developed the custom worn in-the-ear hearing aid became a reality. Further miniaturization has brought the industry to the latest completely in the canal (CIC) models, which are virtually invisible.

Because of demands driven by market forces more powerful than the hearing industry, electronic components have reached a new level of micro-miniaturization. As a consequence, the electronic components used in hearing aids have increased signal processing capabilities requiring very limited space. The development of programmable hearing aids, using either analog or digital processing, has lessened the need for custom electronic design at the manufacturing level, and has allowed the clinician to more directly shape the electro-acoustic response via programmable software. That is, it is no longer necessary for the device to be returned to the manufacturer for hardware changes to arrive at the desired electro-acoustic response.

In direct contrast to electronic advances in the industry, little or no advancement has been realized in shell lab technology. Since the late nineteen sixties, when the custom in-the-ear hearing aid was developed, the materials and the construction techniques have remained virtually unchanged. This industry has taken the dental industry's approach as a means of construction of custom hearing aid design. This device, commonly called a "shell", is slush molded with dental acrylic which has a ninety point Durometer Hardness Shore D. Using a material this hard in the human ear brings to fore the issues of comfort and acoustic performance especially with the ever deeper placement of the hearing instrument into the ear canal. When the acrylic shell design was introduced, hearing instruments were worn in a relatively forgiving cartilaginous portion of the ear canal. Continued micro-miniaturization of electronic components, combined with increased consumer demand for a cosmetically acceptable device, has shifted the placement of the hearing aid into the bony portion of the external auditory canal. This bony canal is extremely sensitive and intolerant of an acrylic shell that is over sized or extended beyond the second anatomical canal bend. Rigid acrylic that does not compress must pivot in reaction to jaw or head movement, thereby changing the angle of attack of the receiver yielding a distorted acoustic response. In addition the pivot action causes displacement of the entire device creating unwanted acoustic feedback. This has necessitated shell modifications reducing the scientific integrity of the original dental technology. Current shell design is thereby reduced to more of a craft than a science. The need for a more compliant shell material has been recognized by both industry and clinical professionals.

As of today, a few manufacturers have attempted all-soft shells as an alternative to acrylic shells, and wearers did report greater comfort and better sound quality. Unfortunately, while rigid acrylic does not lose dimensional stability, soft vinyl materials shrink, turn yellow, and become hard after a relatively short period of wear (the replacement of vinyl material used for BTE earmolds, for example, is recommended on at least a yearly basis). Polyurethane has proven to provide a better acoustic seal than polyvinyl, but has an even shorter wear life (approximately three months). Silicones have a long wear life but are difficult to bond to plastics, a necessary process for the construction of custom hearing instruments. Furthermore, silicone is difficult to modify when the dimensional structure requires alteration for proper fit. To date, then, acrylic has proven to be the only material with long term structural integrity. The fact remains, however, that the entire ear is a dynamic acoustic environment ill-served by a rigid material such as acrylic.

As aforementioned, the current trend for hearing aid placement is to position the instrument into the bony portion of the ear canal extending three millimeters medially from the second directional bend, commonly referred to as "deep insertion technology". Anatomically, the ear canal is defined as the area extending from the concha to the tympanic membrane. It is important to note that the structure of this canal consists of elastic cartilage laterally, and porous bone medially. The cartilaginous portion constitutes the outer one third of the ear canal. The medial one-third of the ear canal is osseous or bony and is oriented forward and downward making it slightly concave as compared to the more cylindrical cartilaginous portion. The average canal is approximately twenty-five millimeters in length but is as much as six millimeters longer on the anteroinferior wall of the osseous canal. The osseous canal, measuring only two-tenths of a millimeter (0.2 mm) in thickness, is much thinner than the cartilaginous canal, measuring five-tenths to one millimeter (0.5 to 1 mm) in thickness. The difference in thickness directly corresponds to the presence of apocrine (cerumenous) and sebaceous glands found only in the fibro-cartilaginous area of the canal. Thus, this thin-skinned poorly-lined area of the bony canal is extremely sensitive to any hard foreign body, such as an acrylic hearing instrument.

Exacerbating the issue of placement of a hard foreign body into the ear canal is the ear canal's dynamic nature. It is geometrically altered by the tempro-mandibular action of the mandible and by changes in head position. This causes elliptical elongation (widening) of the ear canal. These alterations in canal shape vary widely not only from person to person, but also from ear to ear within a person. This canal motion makes it impossible to achieve a comfortable, true acoustic seal with hard acrylic material. When the instrument is displaced by motion, a leakage of sound pressure occurs. This leakage, described by Victoreen as "peripheral leakage", creates an open loop between the receiver and the microphone and relates directly to an electroacoustic distortion commonly known as feedback. This peripheral acoustic leakage (PAL) is a complex resonator made up of many transient resonant cavities. These cavities are transient because they change with jaw motion as a function of time resulting in impedance changes in the ear canal that destroys even the best electroacoustic performance, digital or analog.

The properties of hard acrylic have obvious limitations. These limitations require modification to the hard shell exterior to accommodate anatomical variants and the dynamic nature of the ear canal. The shell must be buffed and polished until comfort is acceptable without significantly compromising acoustic performance. The peripheral acoustic leakage caused by these modifications lead to acoustic feedback (whistling) before sufficient amplification is reached to adequately address the wearer's hearing loss. Additionally, this acoustic leakage causes annoying low frequency sounds to be inadvertently amplified by means of a Helmhotz resonator. Patients commonly report this sensation as "My voice is hollow" or "My head sounds like it is in a barrel."

Furthermore, the hollow shell used in today's hearing aid designs creates internal acoustic feedback pathways, which are unique to each device and ear, causing countless electronic modifications to "tweak" the product to a compromised performance or a "pseudo-perfection." In the industry's efforts to facilitate the fine-tuning of these acoustic anomalies, programmable devices were developed. The intent was to reduce the degree of compromise, but by virtue of their improved frequency spectrum the number of high frequency feedback pathways were increased. As a result the industry still falls well short of an audiological optimum.

As we trace the evolution of earmold technology from the early seventies, it is apparent that venting systems, earmold plumbing, acoustic feedback and occlusion effect have been the subjects of extensive research. Excellent studies by Lybarger, Pascoe, Skinner, Sung, Cox, Killion and others have demonstrated the benefits of venting systems and earmold plumbing. In venting studies by Curran, peripheral acoustic leakage (PAL) was categorized as a venting system called a "slit" vent. The paper points out that both high and low frequency components of the spectrum were affected as opposed to the traditional low frequency roll off which normally occurs with parallel venting. A more recent study by Tecca reiterated the earlier findings of Lybarger in that ITE venting were dramatically affected by the diameter and length of the vent. As we continue with deeper placement of instruments, this knowledge of PAL and venting becomes more critical to a successful fit.

Some references of interest are discussed below. These references are all incorporated herein by reference.

U.S. Pat. No. 4,870,688 to Voroba, Barry, et al.

Voroba describes a patient selected mass produced, non-custom molded form fitting shell with a malleable covering having a hook and twist which in theory precisely conforms to the patient's own ear.

U.S. Pat. No. 4,880,076 to Ahlberg, Carl, et al.

Ahlberg discloses a user-disposable foam sleeve comprising a soft polymeric retarded recovery foam that can be compressed to be freely inserted into the patient's ear and then allowed to expand until secure in the ear canal.

Other patents that may be of interest include the following:

U.S. Pat. No. 5,002,151 to Oliveira, Robert J., et al.;
U.S. Pat. No. 4,607,720 HEARING AID;
U.S. Pat. No. 4,375,016 VENTED EAR TIP FOR HEARING AID AND ADAPTER COUPLER THEREFOR;
U.S. Pat. Nos.: 5,500,902; 4,051,330; 5,430,801; 5,185,802; 5,201,007; 4,937,876; 4,811,402; 4,716,985; 5,659,621; 5,530,763; 5,068,902; and 5,259,032.

Also of interest are published Japanese patent application no. JA61-238198 and Staab, Wayne J. and Barry Finlay, "A fitting rationale for deep fitting canal hearing instruments", HEARING INSTRUMENTS, Vol. 42, No. 1, 1991, pp. 7–10, 48.

BRIEF SUMMARY OF THE INVENTION

The present invention relates generally to custom in-the-ear hearing aids and particularly to a soft elastomer solid within which the electronic components are embedded. The general objective of this invention is to provide a product which is authentic to the shape of the external ear canal, yet compliant enough to compensate for the dynamic properties of the canal.

The specific objectives of this invention are:

1. to provide an instrument that, by virtue of its softness, will not migrate out of the external ear canal with jaw excursion.
2. to provide an instrument that, by virtue of its softness, will remain acoustically sealed with jaw excursion.
3. to provide an instrument that, by virtue of its softness, will not exert pressure on the bony portion of the external ear canal with jaw excursion.
4. to provide an instrument that, by virtue of its softness, will ensure correct receiver orientation during jaw excursion.
5. to provide an instrument that, by virtue of its solidity, will protect the embedded electronic components.
6. to provide an instrument that, by virtue of its solidity, will eliminate the internal air conducted feedback pathway from the receiver to the microphone.
7. to provide an instrument that, by virtue of the solidity, will eliminate the need to tube-mount the receiver, thereby preventing displacement of the receiver within the hearing instrument.

The preferred embodiment of the present invention is a soft-solid device for custom in-the-ear hearing aids. Furthermore, acoustic performance of soft earmolds used in behind-the-ear hearing aids have conclusively proven to be superior and more closely achieve the audiological optimum.

The inventors are currently processing a material that is a blended silicone (such as 10% 35 Durometer silicone (such as Dow MDX4-4210) and 90% 20 Durometer silicone (such as Factor II Realistic A-588)) that accepts bonding to plastic by adhesives. This new material offers better comfort and acoustic performance. This material is the current preferred embodiment of the invention described herein.

A further objective of this soft-solid technology is to produce a completely soft hearing aid through the elimination of the present hard plastic molded faceplate.

BRIEF DESCRIPTION OF THE SEVERAL VIEWS OF THE DRAWINGS

For a further understanding of the nature, objects, and advantages of the present Invention, reference should be had to the following detailed description, read in conjunction with the following drawings, wherein like reference numerals denote like elements and wherein.

DETAILED DESCRIPTION OF THE INVENTION

The preferred embodiment of the present invention is a hearing aid which is substantially solid yet soft. The softness provides comfort and ease of fit. The solidness improves acoustic qualities and allows patients to hear better than with typical hollow hearing aids.

The current preferred embodiment of the invention brings earmold laboratory technology from an acrylic craft, originating from early dental laboratory processes, to a precision science in soft-solid hearing aids. This new approach eliminates the need for "shell" lab technician modifications of existing ear impressions received from the audiologist or hearing specialist. Hence, a more direct method of casting is achieved, yielding greater accuracy of topographical detail of the ear canal in terms of dimensional and geometric characteristics. The end result is a soft device which outperforms current acrylic products in both wearer comfort and acoustic performance.

Figure 1:
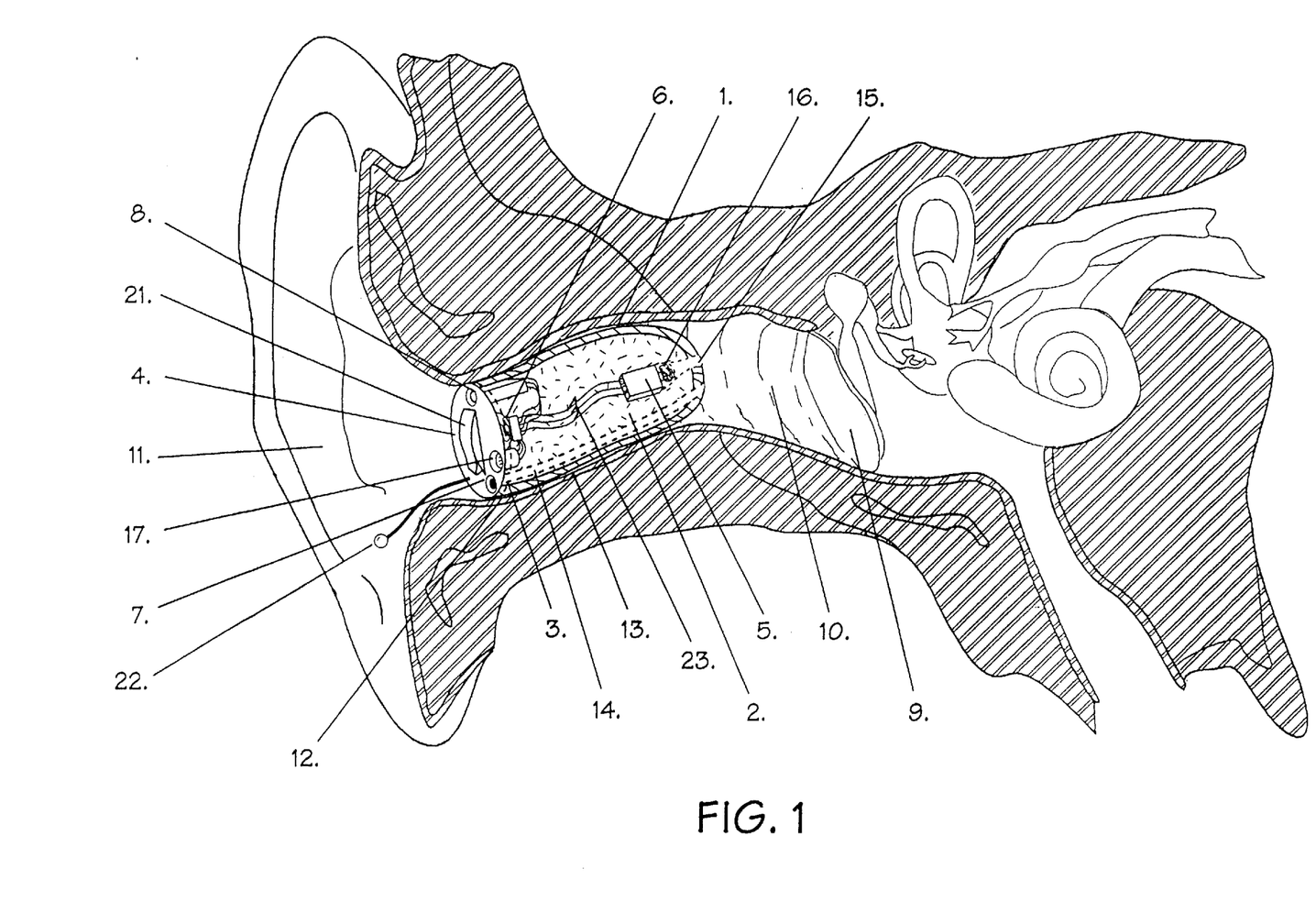
FIG. 1 shows the device of the preferred embodiment of the present invention in a typical human ear from a side perspective.
Figure 2:
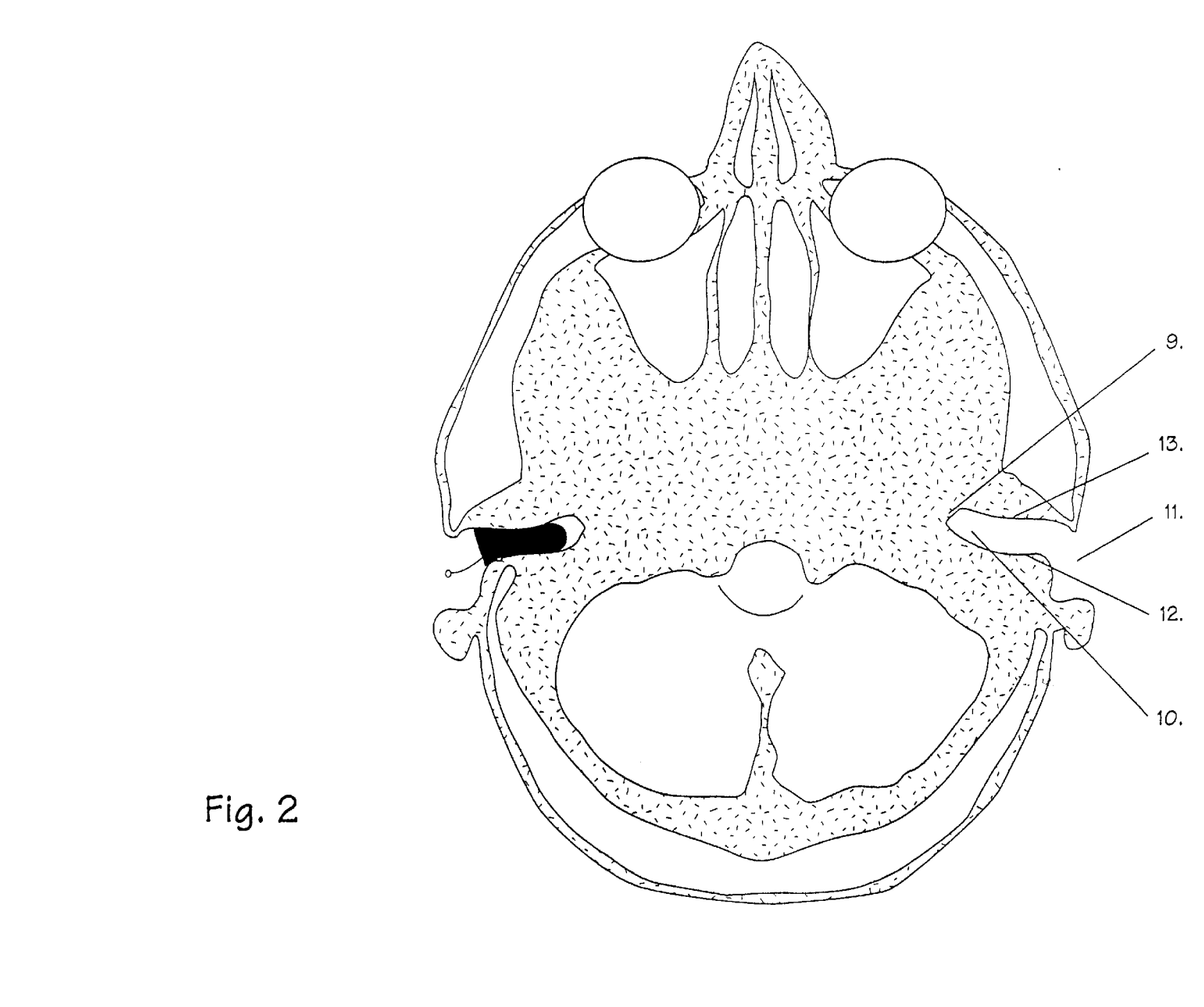
FIG. 2 shows the device graphically illustrated via magnetic resonance imaging (MRI) in a typical human ear as viewed from the top of the head, superior to inferior.
Figure 3:
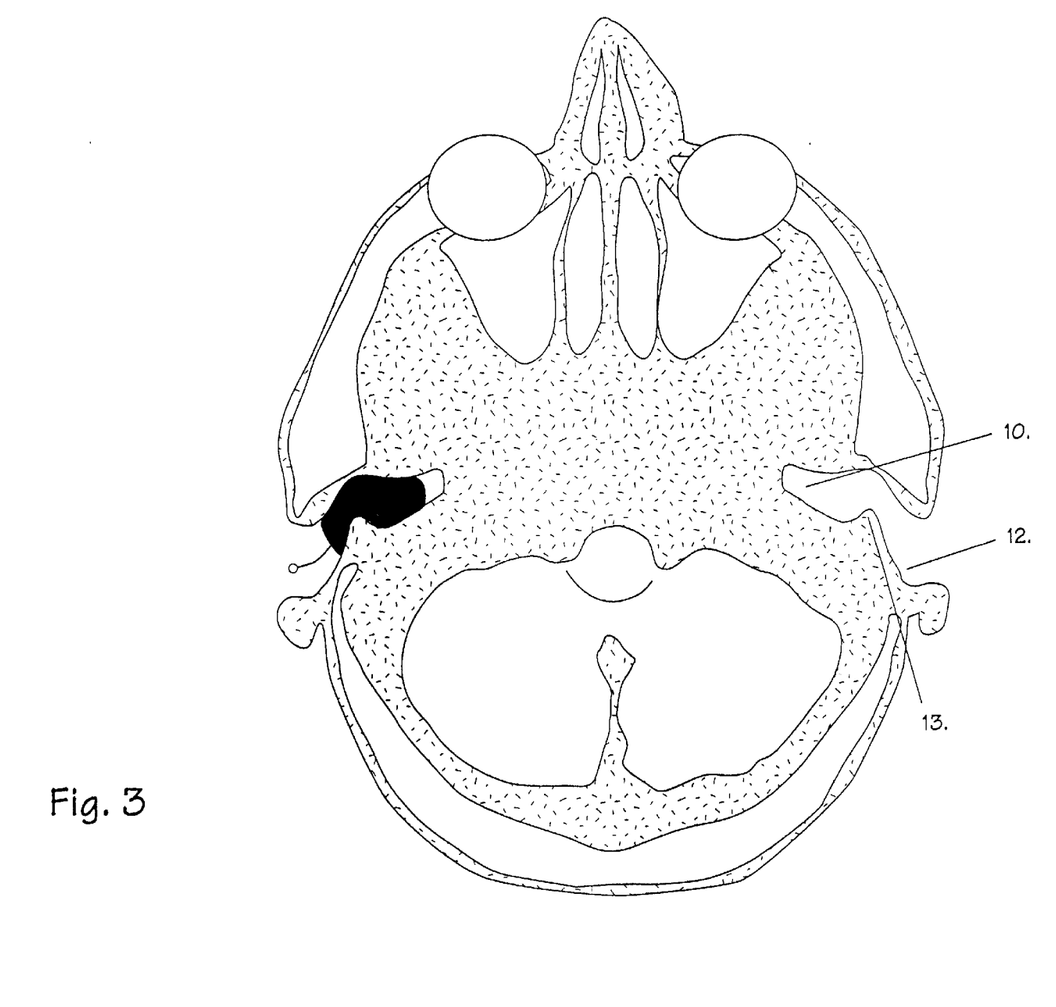
FIG. 3 shows the device as described in FIG. 2 except with an anatomic variant defined as a bulbous ear canal.
Figure 4:
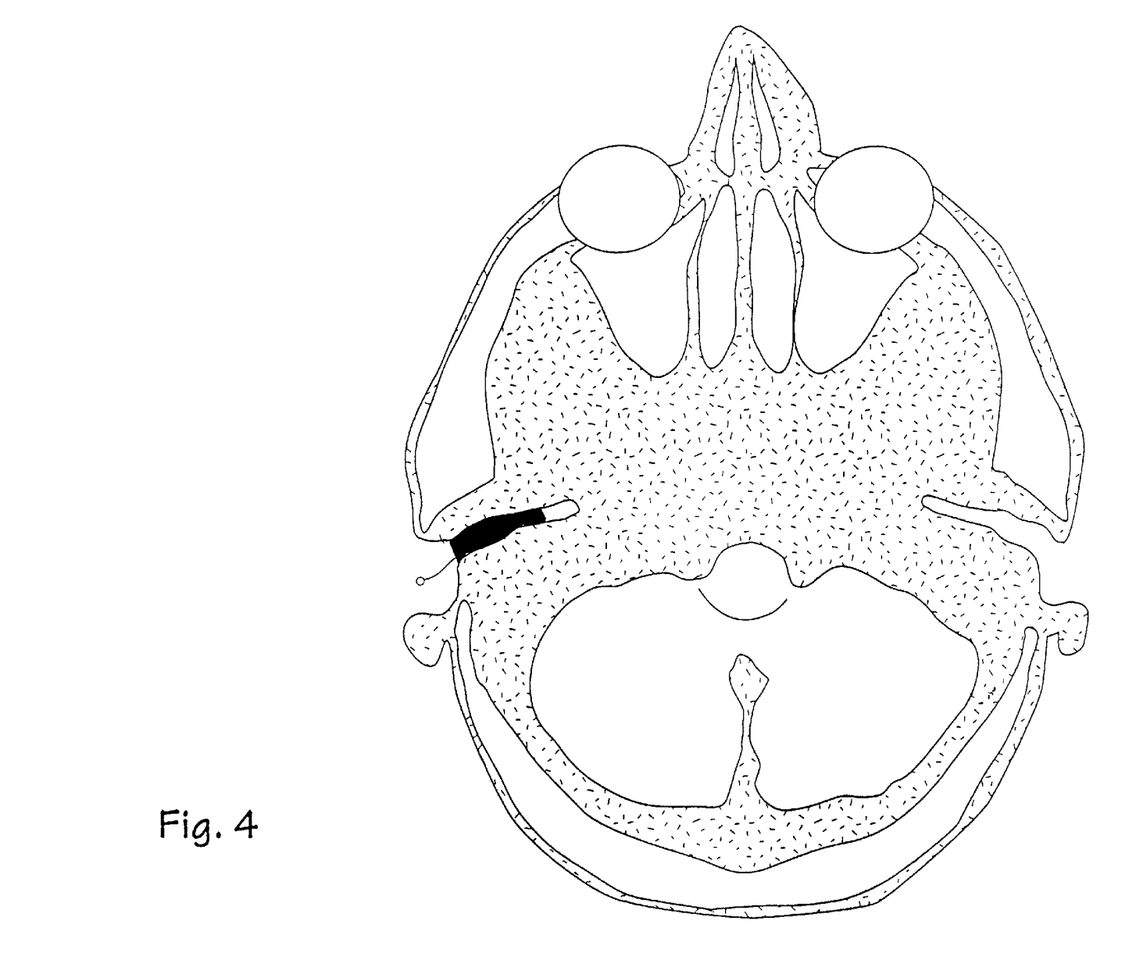
FIG. 4 shows the device as described in FIG. 2 except with an anatomic variant defined as a stenotic ear canal.
Figure 5:
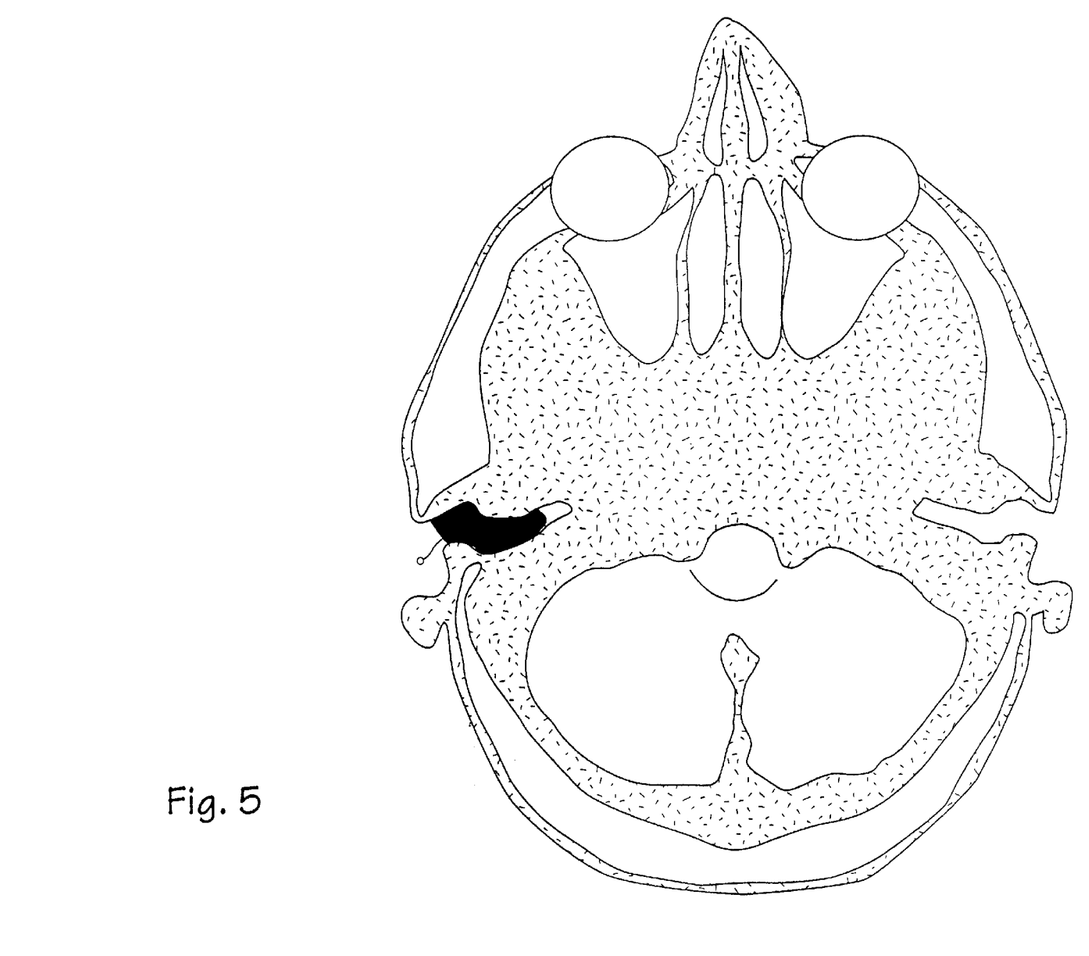
FIG. 5 shows the device as described in FIG. 2 except with an anatomic variant defined as a torturous ear canal.
Figure 6:
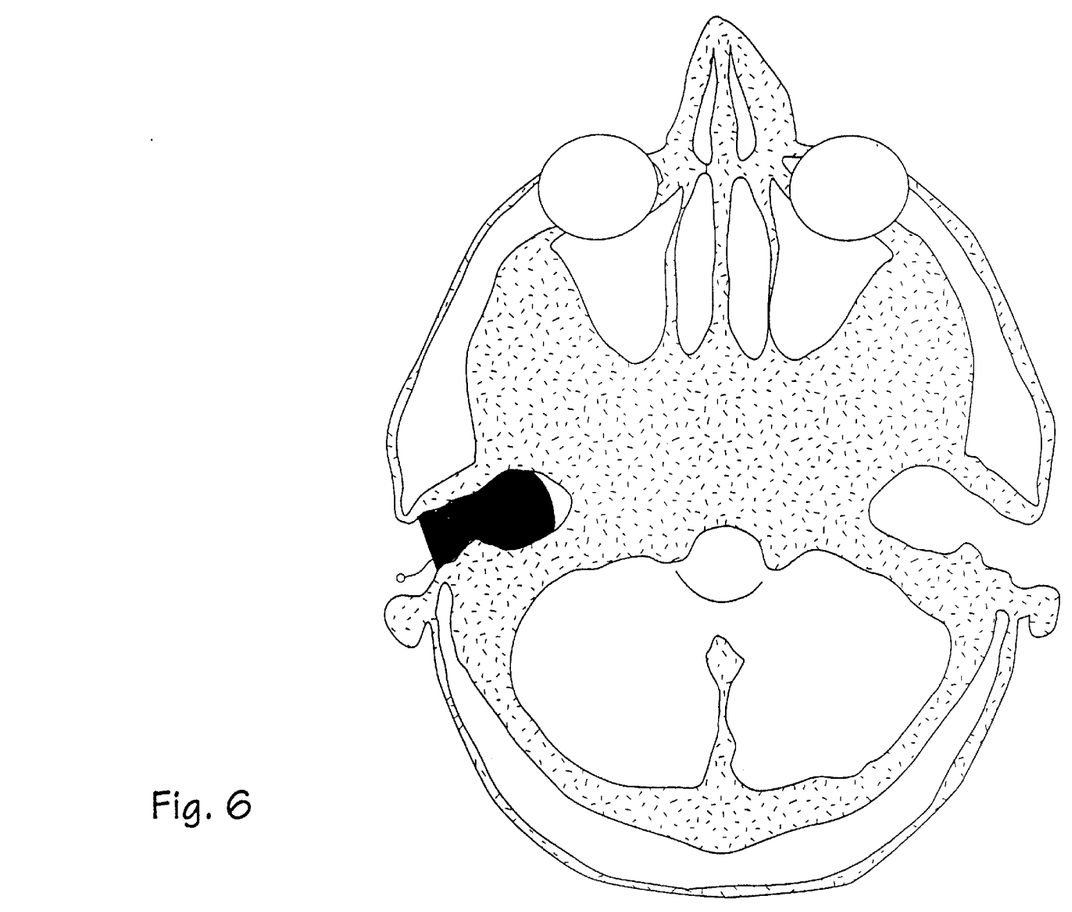
FIG. 6 shows the device as described in FIG. 2 except with an iatrogenic variant demonstrating a post surgical ear canal.
Figure 7:
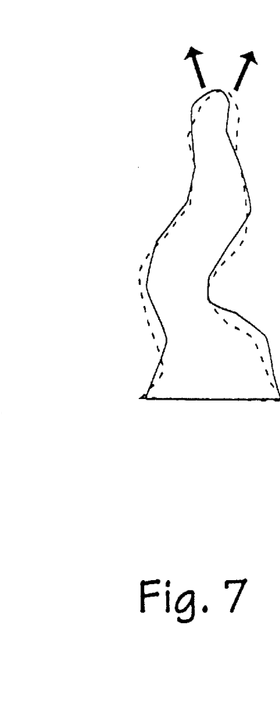
FIG. 7 shows the device as described in FIG. 2 demonstrating ear canal volume change and canal angle variance between the jaw open position and the jaw closed position (dotted)
Figure 8:
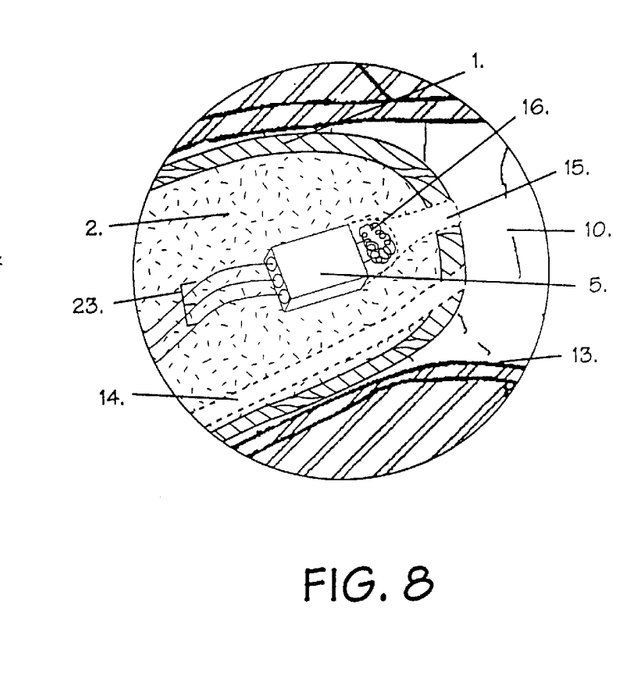
FIG. 8 shows preferred embodiment of the invention including the preferred embodiment of the wax chamber.
Figure 9:
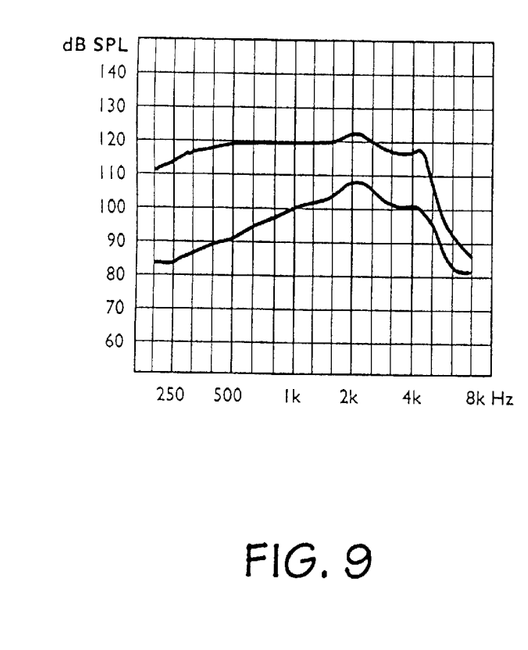
FIG. 9 shows an acoustic illustration of a typical response.
Figure 10:
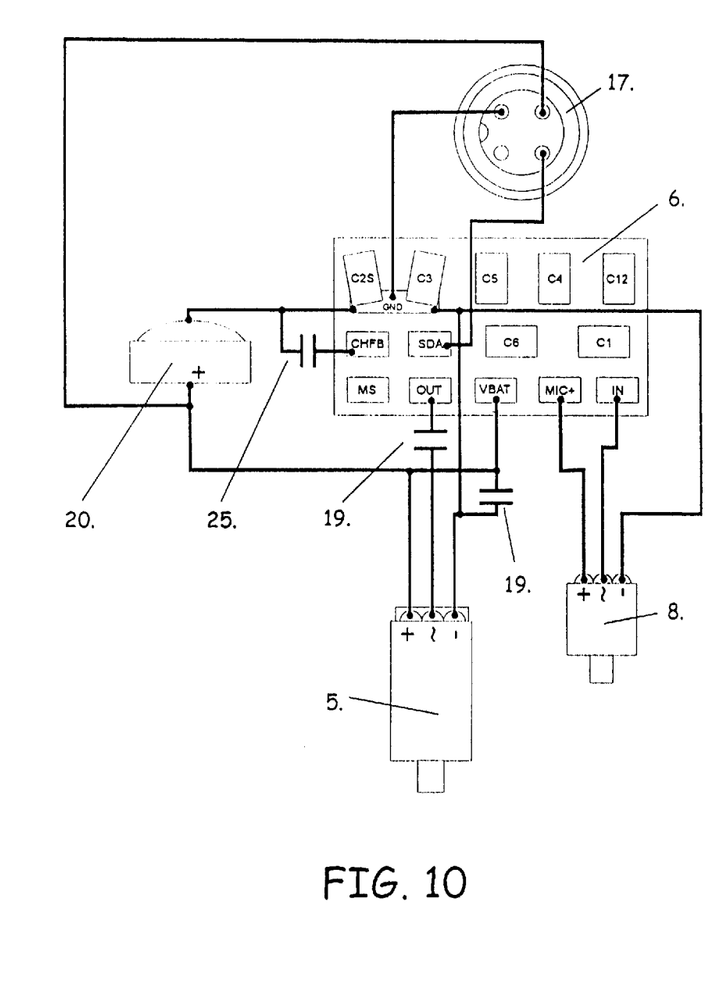
FIGS. 10 and 11 show two typical hearing aid designs being currently produced.
Figure 11:
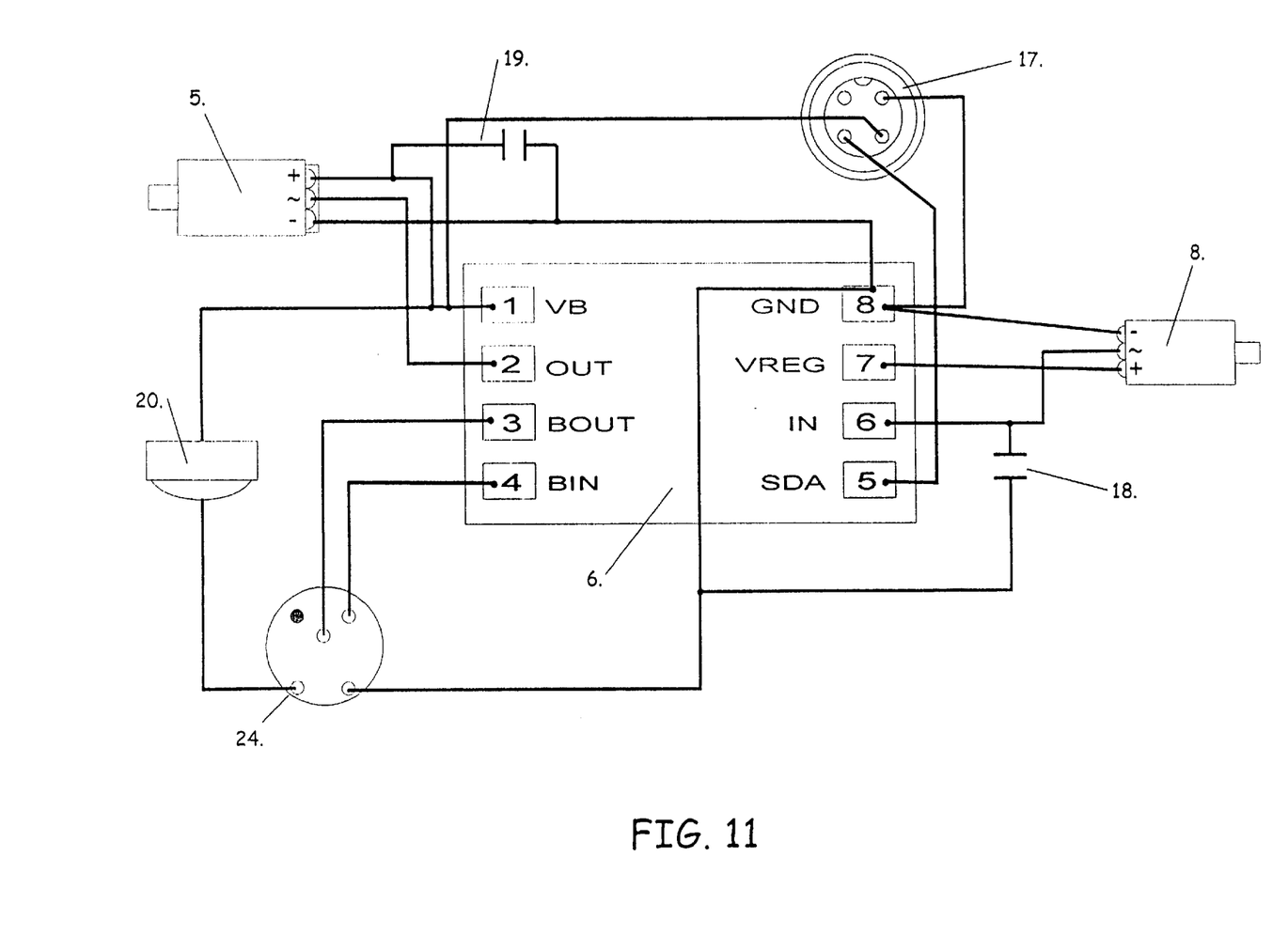

FIG. 1 shows one configuration of a complete device in the human ear from a side perspective. Outer layer 1 is a soft polydimethysilioxane layer of 35 durometer hardness shore A, Dow Corning® MDX4-4210 in the current embodiment. This outer layer acts as a bacteriological barrier and a general surface skin that provides greater resistance to tearing and provides the stiffness for insertion into tortuous ear canals. The thickness of this skin depends on ear size and geometry of the particular ear. The stiffness is selected based on the cross sectional diameter and the shape of the ear canal. A soft center 2 is made of polydimethysilioxane with functional groups and fillers, usually twenty points durometer hardness, shore A, in this case Factor II Realistic™ (A-588). This is as soft as possible and provides the elasticity necessary to occupy the entire external ear canal. Further the soft center elastomer must maintain wall pressure between the device and the ear canal wall 13 from the sagittal plane of the aperture medially to the end of the device. In addition, the composite of layer 1 and center 2 has elastic properties that allow it to flex with jaw excursion without losing its acoustic seal. This flexing serves to eliminate the pivoting of the device, which results in displacement. It particularly serves to prevent peripheral acoustic leakage and acts to eliminate the internal air conduction path between the microphone and the receiver found in traditional hollow hearing aid shells. A bonding agent 3 made of Factor II silicone bonding enhancer (A-320) adheres the soft bodies of layer 1 and center 2 to the plastic faceplate 4, In'Tech® model 10A faceplate, of the device. A typical acoustic receiver 5 can be a Knowles® model ES7653. Amp 6 can be an Etymotic Research model ER-42D K-Amp™ DSD programmable hybrid, populated with capacitors and wired to the battery compartment and other components. A programming socket 17 can be Microtronic CS44 and is used to connect the hearing instrument to the computer programming unit. Microphone 8 can be a Knowles® model TM 3546.

The tympanic membrane 9 is driven by the receiver 5 by means of air conduction in the cavity of air 10 formed by the tympanic membrane 9 and the proximal end of the hearing aid. Sound enters the microphone 8 and is transduced to an electrical signal then transmitted by a five strand, forty-four gauge wire 23 to the amplifier 6. The signal is then conducted by wire and transduced back to an acoustic signal by the receiver 5. The acoustic signal then enters a spherical cavity which extends to a cylindrical tube 15. This cavity is loosely filled with an acoustic medium 16, usually lambs wool or foam, which acts as a wax protection system for the receiver 5, and further serves to smooth out the peaks of the acoustic response. Venting system 14 allows for pressure equalization during swallowing and reduces the low frequency sound spectrum. The vent system 14 is molded in place using a silicone tube and removing it once the soft-solid hearing aid body has completely vulcanized. In a similar manner, the wax guard 15 is molded by a tube and sphere which are withdrawn once the body of the device has cured. Both venting system 14 and wax guard 15 are optional depending on the hearing loss and the physical size and shape of the particular ear being fit.

Other products such as digital phones, pagers and clocks could also be encapsulated for wearing in the ear.

The following materials (typical soft solid material makeup) can be used to make the two-layer body shown in FIG. 1.

Dow Corning® MDX4-4210 Base
Dow Corning® MDX4-4210 Curing Agent
Acetone
Factor II Realistic II (Polydimethylsilioxane with functional groups and fillers)[A-588]
Factor II Silicone Primer [A-304]
Factor II Silicone Bonding Enhancer [A-320]
Audacryl™ RTC Methacrylate Monomer Mixture Audacryl™ RTC Poly Ethyl Methacrylate (clear)

As used herein, the following list contains typical hearing aid circuit components

| | |
|---|---|
| | Tansitor ® 2.2 capacitor |
| | Tansitor ® 0.047 capacitor |
| 4 | In'Tech ® 10A Faceplate |
| 5 | Knowles ® ES7653 receiver |
| 6 | Etymotic Research ER-42D K-Amp ® /DSD programmable hybrid |
| 17 | Microtronic CS44 socket |
| 8 | Knowles ® TM3546 microphone |
| 21 | In'Tech ® 10A Battery Door |
| | RTI ® 10A hard battery boot |
| | Insulated stranded wire |
| 16 | lambs wool or foam |
| | silicone tubing |

TYPICAL EARMOLD PREPARATION

The following procedure is a description of how to make a device similar to that shown in FIG. 1, but without distinct layers 1 and 2—instead, a single soft-solid body is formed in a mold. Initial research shows that this is easier to make than the two-part body shown in FIG. 1 and that this single soft-solid body appears to work just as well. The hardness of the soft-solid body is preferably around 10–55 Durometer, Shore A (more preferably around 15–35 Durometer, Shore A, and most preferably around 20–25 Durometer, Shore A).

For preparation of an impression, a silicone impression of the external ear canal is received from an audiologist or hearing aid specialist. It is preferable that a non-shrinking impression material such as silicone be used since the dimensional stability and elastic memory are crucial to a faithful reproduction of the ear cavity. The use of polymethyl methacrylate is not recommended because of poor dimensional stability and ease of handling, although it may be used. The canal length of the impression should extend at least 3 mm past the second bend of the external auditory meatus. The open mouth ear impression technique is recommended.

Upon receipt, the impression is cut and shaped for the desired shell style. Major characteristics of the ear will not be changed. Detail on the canal extending from the first directional bend to the proximal tip will not be altered. All cutting and shaping should be done at this time except for height. The ear dam string line and minor imperfections are filled with room-temperature-vulcanizing (RTV) silicone with a syringe and allowed to dry. The impression is sprayed with silicone mold release. The impression is dipped repeatedly in acrylic until a 2 mm wall is formed. The acrylic/impression unit is put in hot water for two minutes to cure the acrylic, thereby creating an acrylic investment, The impression is removed from the acrylic investment. The investment is decked down to the desired height.

Electronics are assembled on the plate per CJC instructions with the following differences: A full hard battery boot should be used, and should be sealed completely. Components should not come into contact with the acrylic investment. All wires except for the receiver wires should be secured to the plate.

Wipe plate down with acetone, and allow to dry. Coat plate with primer, and allow about 30 minutes to dry (will turn powdery white). Coat with bonding enhancer, then allow a 30 minutes to dry.

Into the investment, a receiver hole, a vent hole, and a "pouring" hole are drilled. Flashing is removed from the inside of the drilled holes. Alcohol or monomer is used to clear the inside of the investment completely. The receiver tube and the vent tube are pulled into the investment for gross positioning. The investment is positioned onto the plate and Cycobonded. Through the pouring hole the soft elastomer material is injected via a hand syringe. The elastomer filled shell is placed in a pressure pot to remove any air bubbles. The mic and receiver tubes are blocked to ensure they are "water safe." The elastomer filled shell is placed into a pot of water, which is then placed on the stove on a low setting to maintain a water temperature of 120 Degrees Fahrenheit. The pressure pot is then sealed and pressurized with air to approximately 25 pounds per square inch for two hours. The filled shell is removed from the water and allowed to cure overnight. The hearing instrument is now prepared for finishing.

The hearing instrument is now prepared for finishing.

There are several advantages to the present invention. For example, the instrument can flex during jaw motion. Further, the present invention allows insertion into the external ear canal past the second directional bend whereby the instrument will be residing in the bony canal without causing discomfort or associated sores or pain to the patient. The present invention allows successful fitting of traditionally difficult ear canal types: the ear canal which is narrow at the aperture, and bulbous just medial to the aperture; the tortuous ear canal; the stenotic ear canal; and the surgical ear canal. The present invention facilitates the delivery of the complete sound spectrum, particularly the high frequencies usually lost in traditional acrylic shell hearing aids due to peripheral leakage, hollow shell containing receiver, and internal air conduction feedback pathway from the receiver. The present invention reduces mechanical breakage usually caused by shock and vibration.

The present invention, because it is processed by means of male to female cavity whereby the final product is cast more accurately, eliminates buffing, waxing, and other means of impression modification inherent to current shell manufacturing procedures.

The present invention is authentic to the topography of the ear canal, and resistant to lateral migration that necessitates frequent repositioning of the traditional non-compliant shell.

The present invention creates an acoustic seal that will reduce peripheral leakage and allow for greater gain and sound pressure before feedback.

The present invention creates a less reverberant environment that will allow for greater gain and sound pressure before feedback.

The present invention allows for precise uniform vent diameters thereby giving predictable electroacoustic responses.

The present invention eliminates receiver mounting by silicone tube, thereby eliminating receiver tube displacement and concomitant Helmholz resonation.

The present invention, by elimination of the receiver tube, will allow for the easy installation and changing of an effective wax guard system.

The present invention enables deeper insertion into the ear canal, providing closer proximity to the tympanic membrane, thus decreasing residual volume and increasing compliance. Therefore, greater perceived power and greater high frequency response will be realized without resorting to increasing the gain of the instrument.

The present invention will accommodate additional personal communication devices such as telephones, pagers, memo recorders, and two-way communication devices.

The present invention can contain a receiver without additional components that will interface with personal communication devices such as external telephones, pagers, memo recorders, and two-way communication devices.

The present invention will have a long wear life of two years or longer with daily wear in the ear and the recommended cleaning.

The present invention can be made with a bladder mounted in the center to be filled by extrusion of a soft material, by means of a syringe and then through an orifice or other means, once in the patient's ear and allowed to vulcanize to a soft hardness of less than 35 points, Durometer Hardness, Shore A.

The present invention can be made with a bladder mounted external to the electronic components to be filled by extrusion of a soft material, by means of a syringe and then through an orifice or other means, once in the patient's ear and allowed to vulcanize to a soft hardness of less than 35 points, Durometer Hardness, Shore A.

The present invention can flex during insertion while passing through the narrow opening of the external ear canal and preferably has sufficient elastic memory to return to its original shape thereby occupying the complete ear canal volume medially from the aperture to the proximal end of the hearing device.

| | |
|---|---|
| 3 | bonding agent |
| 4 | faceplate |
| 5 | receiver |
| 6 | K-amp amplifier |
| 7 | vent hole in faceplate 4 |
| 8 | microphone |
| 9 | TM |
| 10 | cavity |
| 11 | concha |
| 12 | sagittal plain or aperture of ear canal |
| 13 | external ear canal wall |
| 14 | vent in hearing aid |
| 15 | wax guard |
| 16 | acoustic media (such as lambs wool) in wax guard |
| 17 | programming socket |
| 18 | input decoupling capacitor |
| 19 | output decoupling capacitor |
| 20 | battery |
| 21 | battery door |
| 22 | extraction cord |
| 23 | 44 gauge 5 strand wire |
| 24 | volume control |
| 25 | CHFB capacitor |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

We claim:

1. A completely in-the-ear hearing device for a patient, the device comprising:
   (a) a solid polymeric hearing device body that is shaped to fit the patient's ear canal; and
   (b) a hearing aid circuit that includes a plurality of electronic hearing aid components, including at least transducers and a volume control forming an amplifier network, the body including a supporting interface portion comprised of soft-solid polymeric material that is of sufficient thickness to closely conform to both the ear canal and at least the amplifier network that is embedded into the body;
   c) wherein the body is made of a soft polymeric elastomer and the body has a Durometer Hardness, Shore A, of less than 40 points.

2. A device as in claim 1, wherein the body includes an outer portion and an inner portion, and at least 90% of the body has a Durometer Hardness, Shore A, of less than 25 points and comprises the inner portion.

3. A device as in claim 1, wherein the body includes an outer portion and an inner portion, and at least 80% of the body has a Durometer Hardness, Shore A, of less than 35 points and comprises the inner portion.

4. A device as in claim 1, wherein the body includes an outer portion and an inner portion, and the inner portion is gel elastomer filled and has a Durometer Hardness, Shore A, of less than 35 points.

5. The device of claim 1, wherein the body occupies at least 70% of the volume of the hearing device not occupied by the amplifier network.

6. The device of claim 1, wherein the body occupies at least 80% of the volume of the hearing device not occupied by the amplifier network.

7. The device of claim 1, wherein the body occupies at least 90% of the volume of the hearing device not occupied by the amplifier network.

8. The device of claim 1, wherein the body occupies at least 99% of the volume of the hearing device not occupied by the amplifier network.

9. The device of claim 1, wherein the body is non-absorbent, and, therefore, impervious to cerumen.

10. The device of claim 1, wherein the body shields, by means of encapsulation, the electronic components from the hostile environment of the ear which usually causes corrosion of exposed connections.

11. A completely in-the-ear hearing device for a patient, the device comprising;
    (a) a soft, solid polymeric hearing device body that is shaped to fit the patient's ear canal;
    (b) a hearing aid circuit that includes a plurality of electronic hearing aid components the body including a supporting interface portion comprised of soft-solid polymeric material that is of sufficient thickness to closely conform to both the ear canal and at least one of the electronic hearing aid components; and
    (c) wherein the body is made of a soft polymeric elastomer and the body has a Durometer Hardness, Shore A, of less than 40 points.

12. The device of claim 11 wherein the body is made of a soft polymeric elastomer that has a Durometer hardness, shore A, of between about 10–40 points.

13. The device of claim 11 wherein the body is made of a soft polymeric elastomer that has a Durometer hardness, shore A, of between about 15 to 35 points.

14. The device of claim 11 wherein the body is made of a soft polymeric elastomer that has a Durometer hardness, shore A, of between about 20–25 points.

15. The device of claim 11 wherein the body is made of a soft polymeric elastomer that has a Durometer hardness, shore A, of between about 15–20 points.

16. A device as in claim 11, wherein the body includes an outer portion and an inner portion, and the inner portion is gel elastomer filled and has a Durometer Hardness, Shore A, of less than 35 points.

17. The device of claim 11, wherein the body is non-absorbent, and, therefore, impervious to cerumen.

18. The device of claim 11, wherein the body shields, by means of encapsulation, the electronic components from the hostile environment of the ear which usually causes corrosion of exposed connections.

19. The device of claim 11 wherein one of the embedded components is a transducer.

20. a completely in-the-ear hearing device for a patient, the device comprising:
  (a) a soft, solid polymeric hearing device body that is shaped to fit the patient's ear canal;
  (b) a plurality of hearing aid components that include a hearing aid circuit, the body including a supporting interface portion comprised of soft-solid polymeric material that is of sufficient thickness to closely conform to both the ear canal and at least one of the hearing aid components, at least a second component being connected to said first component; and
  (c) wherein the supporting interface portion is made of a soft elastomer with a Durometer Hardness, Shore A, of less than 40 points.

21. The device of claim 20 wherein the body is made of a soft polymeric elastomer that has a Durometer hardness, shore A, of between about 10–40 points.

22. The device of claim 20 wherein the body is made of a soft polymeric elastomer that has a Durometer hardness, shore A, of between about 15 to 35 points.

23. The device of claim 20 wherein the body is made of a soft polymeric elastomer that has a Durometer hardness, shore A, of between about 20–25 points.

24. The device of claim 20 wherein the body is made of a soft polymeric elastomer that has a Durometer hardness, shore A, between about 15–20 points.

25. A device as in claim 20 wherein the body includes an outer portion and an inner portion, and the inner portion is gel elastomer filled and has a Durometer Hardness, Shore A, of less than 35 points.

26. The device of claim 20, wherein the body is non-absorbent and therefore, imperious to cerumen.

27. The device of claim 20, wherein the body shields, by means of encapsulation, the electronic components from the hostile environment of the ear which usually causes corrosion of exposed connections.

28. The device of claim 20 wherein one of the embedded components is a transducer.

29. The completely in-the-ear hearing device for a patient, the device comprising:
  a) a soft-solid polymeric hearing device body that is shaped to fit the patient's ear canal;
  b) a hearing aid circuit that includes a plurality of electronic hearing said components, including at least transducers and a volume control forming an amplifier network the body including a supporting interface portion comprised of soft-solid polymeric material that is of sufficient thickness to closely conform to both the ear canal and at least one of the transducers; and
  c) wherein solid portion of the body is made of a soft-solid polymeric elastomer with a Durometer Hardness, Shore A, of less than 40 points.

* * * * *